United States Patent [19]
Nakamura

[11] Patent Number: 5,441,505
[45] Date of Patent: Aug. 15, 1995

[54] MEDICAL LOCATING APPARATUS

[75] Inventor: Katsushige Nakamura, Tokyo, Japan

[73] Assignee: Mitaka Kohki Co., Ltd., Tokyo, Japan

[21] Appl. No.: 187,979

[22] Filed: Jan. 28, 1994

[30] Foreign Application Priority Data

Jan. 28, 1993 [JP] Japan .................................. 5-031123

[51] Int. Cl.$^6$ ............................................. A61B 19/00
[52] U.S. Cl. .................................. 606/130; 128/653.1; 414/917
[58] Field of Search ..................... 606/1, 130; 604/116; 128/653.1; 414/917; 901/15, 41, 48; 378/208, 205

[56] References Cited

U.S. PATENT DOCUMENTS

| 3,338,235 | 8/1967 | Gordon | 606/130 |
| 4,571,243 | 2/1986 | Froning et al. | 606/130 |
| 5,004,457 | 4/1991 | Wyatt et al. | 606/130 |
| 5,257,998 | 11/1993 | Ota et al. | 128/653.1 |

FOREIGN PATENT DOCUMENTS

| 0469966 | 7/1991 | European Pat. Off. | 606/130 |
| 0482439 | 1/1970 | Switzerland | 606/130 |

OTHER PUBLICATIONS

Japanese Patent Gazette of Pre-Examination of Patent Publication No. Sho 62-327.

Primary Examiner—Stephen C. Pellegrino
Assistant Examiner—Glenn Dawson
Attorney, Agent, or Firm—Lowe, Price, Leblanc & Becker

[57] ABSTRACT

A medical locating apparatus including a main parallel link and subsidiary parallel links are formed by first second and third links, first, second and third sub-links and a crank member, in which the respective links are interlocked with corresponding parallel links, respectively. Accordingly, clutch means need not be disposed to all of the connection shafts of the links, but they may be located close to a pivot at a relatively low position, to a connection shaft connecting the first auxiliary link with the first sub-link and to a connection shaft connecting the second auxiliary link with the second sub-link. Thus, the links need not be operated by the respective heavy clutches. The present apparatus enjoys excellent operability, and such a structure is also advantageous from the standpoint of stability of the entire apparatus.

2 Claims, 5 Drawing Sheets

MEDICAL LOCATING APPARATUS

BACKGROUND OF THE INVENTION

1. Field of the Invention

This invention relates to a medical locating apparatus, particularly to a medical locating apparatus which can suitably be used in brain surgery.

2. BACKGROUND OF THE RELATED ART

As CT scanners and MRI scanners are becoming very popular, neurosurgery has encountered a turning point. Namely, the conventional diagnostic imaging such as cranial plain roentgenography and cerebral angiography are now predominantly being replaced by the three-dimensional diagnostic imaging based on computerized analysis data in the field of brain surgery.

In order to reproduce such locational information specified on the image of CT scanning and the like, a medical locating apparatus which locates the site which needs surgical operation, as disclosed, for example, in Japanese Provisional Patent Publication No. 327/1987, is employed. The medical locating apparatus of the disclosure consists of a plurality of arms provided on a bed, a plurality of potentiometers disposed to the joints of the respective arms and an indicating unit disposed at the tip of the arm, by which the site to be operated is detected based on the signal from the potentiometers.

However, since the arms in such conventional medical locating unit are designed to be moved via the respective joints, clutch means must be provided on all of the joints so as to stop the entire locating apparatus. To dispose a heavy clutch means at a high position near the indicating unit is not preferred in view of operability and stability of the locating apparatus.

Meanwhile, since the angles of the respective joints are detected by the potentiometers, the apparatus are not only required to have an A/D converter but also readily affected by the temperature change.

Further, since the weight of each arm is not well-balanced, operation of the arms requires a great operating physical force, presenting poor operability, disadvantageously.

SUMMARY OF THE INVENTION

This invention was accomplished noting such prior art technique and provides a medical locating apparatus which has excellent operability and requires neither clutch means to the joint which is brought close to the patient nor A/D conversion, and which is not affected by the temperature change.

In order to attain the intended object as described above, the medical locating apparatus according to this invention comprises:

- a first link pivotally supported intermediate its ends at a pivot by said first support;
- a second link pivotally supported at an upper end portion of said first link;
- a third link pivotally supported at a distal end portion of said second link, and rotatable about a longitudinal axis;
- a connection shaft connecting said first link with said second link;
- a crank member pivotally supported at said connection shaft;
- a first auxiliary link and a second auxiliary link, both pivotally supported at respective first end portions at a lower end portion of said first link;
- a first sub-link, disposed to be parallel with said first link, connecting a second end portion of said first auxiliary link with a second end portion of said second auxiliary link;
- a second sub-link, disposed to be parallel with said first link, connecting the second end portion of said second auxiliary link and a first end portion of said crank member;
- a third sub-link, disposed to be parallel with said second link, connecting a proximate end portion of said third link with a second end portion of said crank member; an indicating unit mounted at a lower end of the third link;
- first and second magnetic clutches and first and second rotary encoders, respectively provided at said pivot and at the connection shaft connecting said first auxiliary link with said first sub-link for enabling rotational engagements thereat;
- a third magnetic clutch provided at the connection shaft connecting said second auxiliary link with said second sub-link for enabling engagement therebetween; and
- rotary encoders provided at the connection shaft connecting said second link with said third link, at the longitudinal axis of said third link, and at a rotary shaft of said indicating unit for providing outputs corresponding to their respective rotations, respectively.

The locating unit according to another aspect of the invention further comprises a first counterweight provided on a second end of said first auxiliary link to protrude horizontally therefrom and a second counterweight provided on one end portion of said second auxiliary link to protrude upwardly therefrom;

said firsts counterweight and said second counterweight interlocking with said first auxiliary link and said second auxiliary link, respectively.

Incidentally, in the above and following descriptions, while the expression "link" substantially means the numbered link arm, it indirectly also means the linkage including the link arm; and the expression "to pivot" means that the both end portions of the link are swung like a seesaw on the fulcrum assumed at the middle thereof, whereas the expression "to rotate" means that the link rotates on the longitudinal axis thereof like a drill.

The medical locating unit includes first to third links, first to third sub-links and a crank member constituting a main parallel link and subsidiary parallel links. Since the respective links are interlocked respectively with the corresponding parallel links, clutch means need not be disposed to all of the shafts connecting the links, but only to the pivot locating at a relatively low position, to the connection shaft connecting a first auxiliary link with the first sub-link and to the connection shaft connecting a second auxiliary link with the second sub-link. Accordingly, the links need not be operated by the respective heavy clutches, the present apparatus enjoys excellent operability, and such constitution is also preferred from the standpoint of stability of the entire apparatus.

Further, since the angles of the links are detected by rotary encoders which require no A/D conversion and are not affected by temperature changes, the present apparatus also enjoys excellent locating accuracy.

The locating apparatus also includes a first counter weight and a second counter weight provided to project horizontally from the other end of the first auxiliary link and upward from one end portion of the second auxiliary link to pivot interlocking therewith, respectively, the links can be operated with a very small operating physical force, providing excellent operability.

The gist of the invention is not limited to the above description, and the objects of the invention together with the advantages, features and applications thereof will be apparent by reading the following description taken in conjunction with the attached drawings. It should be understood that suitable modifications or variations without departing from the spirit of the invention are all included in the scope of the present invention.

DESCRIPTION OF THE PREFERRED EMBODIMENTS

Figure 1:
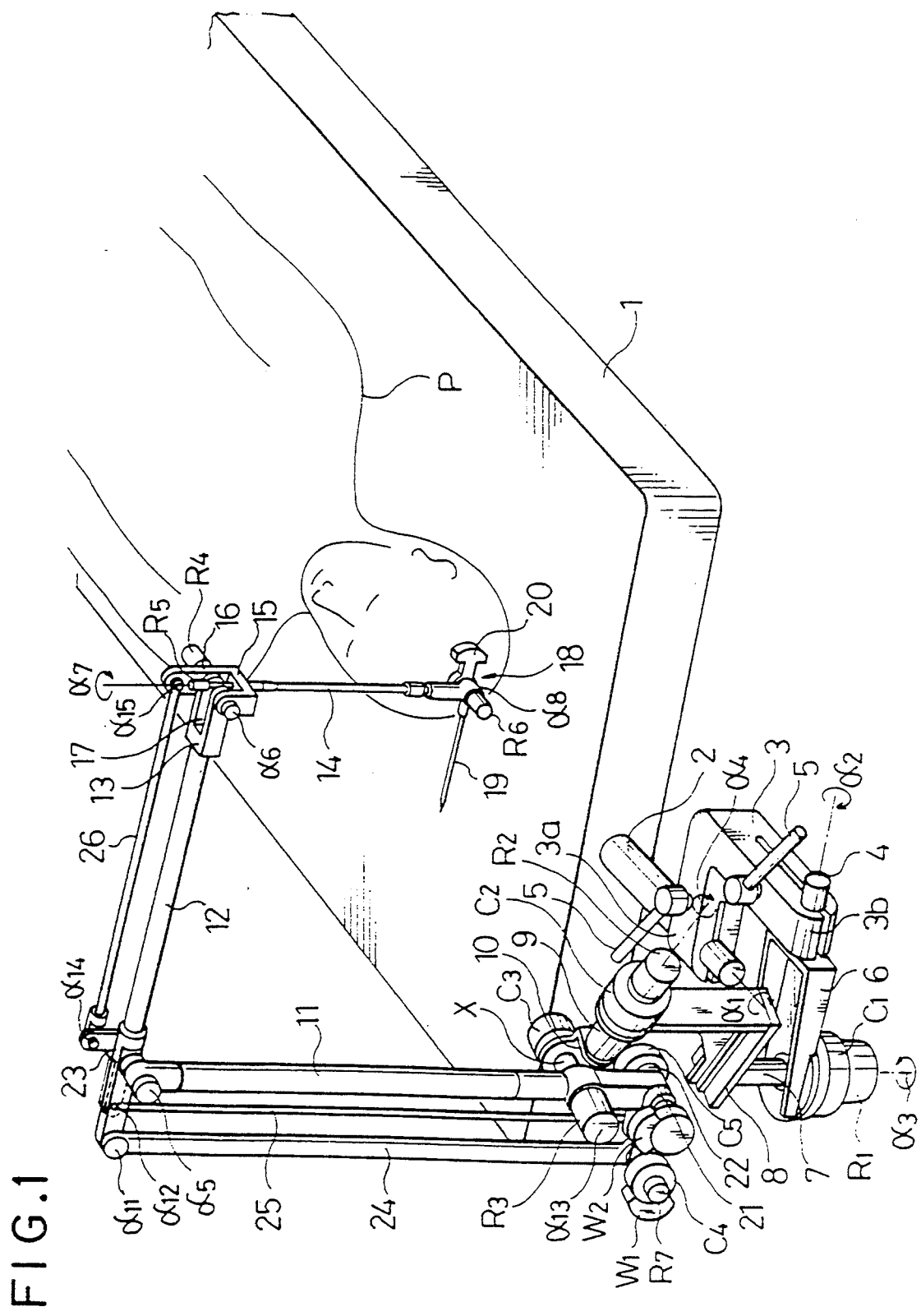
FIG. 1 shows perspectively a medical locating apparatus according to one embodiment of the invention.
Figure 2:
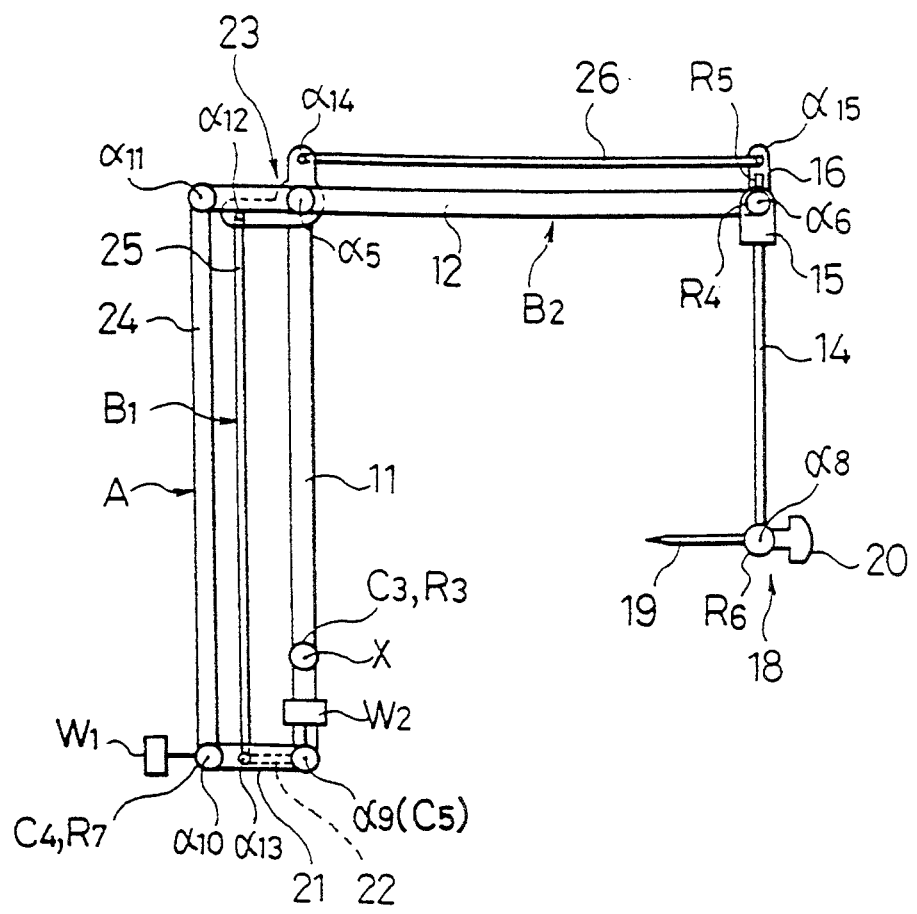
FIG. 2 shows schematically in side view the structure above and including the first link.

An embodiment of the invention will be described below referring to the attached drawings. A patient P lies on a bed 1. (In FIG. 1, the bed 1 is depicted extremely schematically.) A horizontal shaft 2 is fixed to the head end of the bed 1 to be parallel with the longitudinal direction of the bed 1. The horizontal shaft 2 is secured between a pair of jaws 3a, consisting of an upper jaw and a lower jaw, of an L-shaped metal fitting 3. Meanwhile, another horizontal shaft 4 is secured between the other pair of jaws 3b, also consisting of an upper jaw and a lower jaw, of the L-shaped metal fitting 3 to be parallel with the transversal direction of the bed 1. The clamping force of these two pairs of jaws 3a,3b can be adjusted by levers 5, respectively, so that the horizontal shafts 2,4 can be rotated on the longitudinal axes $\alpha_1$, $\alpha_2$, respectively.

A first bracket 6 is fixed to the horizontal shaft 4 extended parallel to the transverse direction of the bed 1, and a perpendicular shaft 7, which is rotatable on the axis $=_3$ thereof, is disposed on the first bracket 6. On the perpendicular shaft 7 are disposed a magnetic clutch $C_1$ and a rotary encoder $R_1$. The angles in the apparatus of the invention are all detected by rotary encoders which require no A/D conversion and are little affected by the temperature. A second bracket 8 is also secured on the upper end of the perpendicular shaft 7, and another horizontal shaft 9, which is rotatable on the axis $\alpha_4$, is supported on the second bracket 8. The horizontal shaft 9 is also provided with a magnetic clutch $C_2$ and a rotary encoder $R_2$. A third bracket 10 having an L-shaped cross section is provided at the other end of the horizontal shaft 9.

A vertical first link 11 is pivotally supported at a point intermediate its ends at a pivot X mounted to on the third bracket 10. A magnetic clutch $C_3$ and a rotary encoder $R_3$ are provided on the pivot X. A second link 12 is pivotally supported at a point intermediate its ends to the upper end portion of the first link 11 by a connection shaft $\alpha_5$. A tip metal fitting 13 is attached to the tip of the second link 12, and a pivotal metal fitting 15 is pivotally supported on the connection shaft a $\alpha_6$ disposed to the tip metal fitting 13, the pivotal metal fitting 15 being secured at the middle of a third link 14. The connection shaft $\alpha_6$ is also provided with a rotary encoder $R_4$. The third link 14 is attached to the pivotal metal fitting 15 to be rotatable on the longitudinal axis $\alpha_7$ thereof. A lever 16 is formed integrally with the pivotal metal fitting 15 to project upward therefrom, on which a rotary encoder $R_5$ for detecting the rotational amount of the third link 14 is mounted. (It should be noted, however, that the rotary encoder $R_5$ is depicted intentionally smaller than the actual relative size for clearer understanding of the relationship with other parts.) Incidentally, the tip metal fitting 13 has a notch 17 for avoiding interference with the upper end portion of the third link 14.

An indicating unit 18 is pivotally supported by a connecting shaft $\alpha_8$ as a rotary shaft to the lower end portion of the third link 14. The indicating unit 18 is provided with an indicating needle 19 and a counter weight 20 on each side of the connecting shaft $\alpha_8$, so that the weight of the indicating needle 19 and that of the counter weight 20 may be balanced at the connection. shaft $\alpha_8$. The connection shaft $\alpha_8$ is provided with a rotary encoder $R_5$. The main link system is as described above, and sub-link systems are combined therewith.

A first auxiliary link 21 and a second auxiliary link 22 are pivotally supported at one end portions thereof on the connection shaft $\alpha_9$ provided on the lower end of the first link 11, respectively, the former being longer than the latter. A crank member 23 is also pivotally supported on the connection shaft $\alpha_5$ connecting the first link 11 and the second link 12. The connection shaft $\alpha_{10}$ provided at one end portion of the first auxiliary link 21 and the connection shaft $\alpha_{11}$ provided at the other end portion of the second link 12 are connected by a first sub-link 24 which is parallel with the first link 11. The connection shaft $\alpha_{10}$ is provided with a magnetic clutch $C_4$ and a rotary encoder $R_7$. A first counterweight $W_1$ which can be pivoted interlocking with the first auxiliary link 21 is provided on the magnetic clutch $C_4$, disposed on the other end of the first auxiliary link 21, to protrude in the horizontal direction. A second counterweight $W_2$ which can be pivoted interlocking with the second auxiliary link 22 is connected to on the connection shaft $\alpha_9$ provided at one end portion of the second auxiliary link 22. The counterweight $W_2$ is provided on the side of the first auxiliary link 21 and connected to the connection shaft $\alpha_9$ of the second auxiliary 22 with a shaft (not shown) which penetrates the first auxiliary link 21. The connection shaft $\alpha_{13}$ provided at the other end portion of the second auxiliary link 22 and the connecting shaft $\alpha_{12}$ disposed at one end portion of the crank member 23 are connected by a second sub-link 25 which is parallel with the first link 11. The connection shaft $\alpha_9$ is provided with a magnetic clutch $C_5$. Further, the connection shaft $\alpha_{14}$ provided at the other end portion of the crank member 23 and the connecting shaft $\alpha_{15}$ of the lever 16 of the rotary metal fitting 15 are connected by a third sub-link 26 which is parallel with the second link 12.

As described above, in the apparatus according to this embodiment, the connection shaft $\alpha_5 \rightarrow$ connection shaft $\alpha_9 \rightarrow$ connection shaft $\alpha_{10} \rightarrow$ connection shaft $\alpha_{11}$ constitute a main parallel link A; the connection shaft $\alpha_5 \rightarrow$ connection shaft $\alpha_9 \rightarrow$ connection shaft $\alpha_{13} \rightarrow$ connection shaft $\alpha_{12}$ constitute a first subsidiary parallel link $B_1$; and the connection shaft $\alpha_5 \rightarrow$ connection shaft $\alpha_6 \rightarrow$ connection shaft $\alpha_{15} \rightarrow$ connection shaft $\alpha_{14}$ constitute a second subsidiary parallel link $B_2$.

Figure 3:
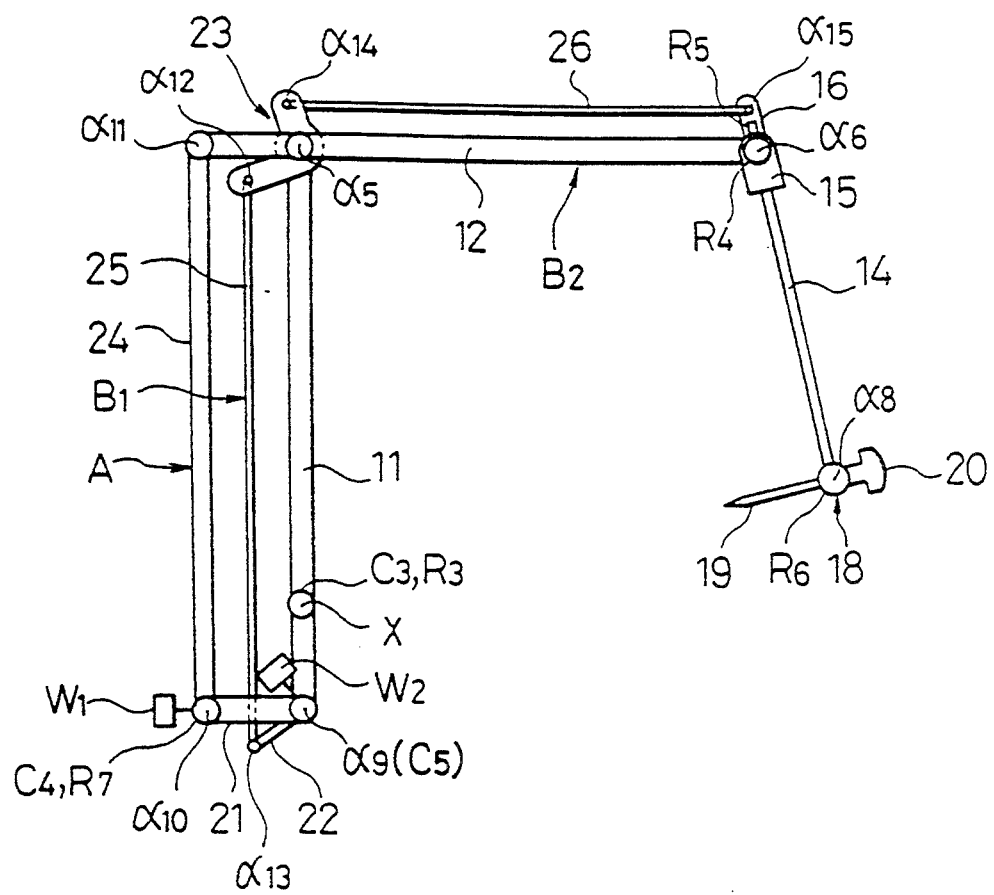
FIG. 3 shows schematically in side view the structure shown in FIG. 2, in which the third link is pivoted.

The action of the mechanism will now be described. The structure above and including the first link 11 is designed to be rotatable in the vertical and horizontal directions with the aid of the shafts $\alpha_1$ to $\alpha_4$. Referring now only to the action of the sub-link system, when the third link 14 is pivoted on the connection shaft $\alpha_6$, as shown in FIG. 3, the shape of the second subsidiary parallel link $B_2$, and that of the first subsidiary parallel link $B_1$ are modified, and the amount of modification (i.e. the pivoted angle of the third link 14) can be detected by the rotary encoder $R_4$. Further, this motion can be locked by the magnetic clutch $C_5$. The third link 14 can be operated with a small operating physical force with the aid of the second counter weight $W_2$.

Figure 4:
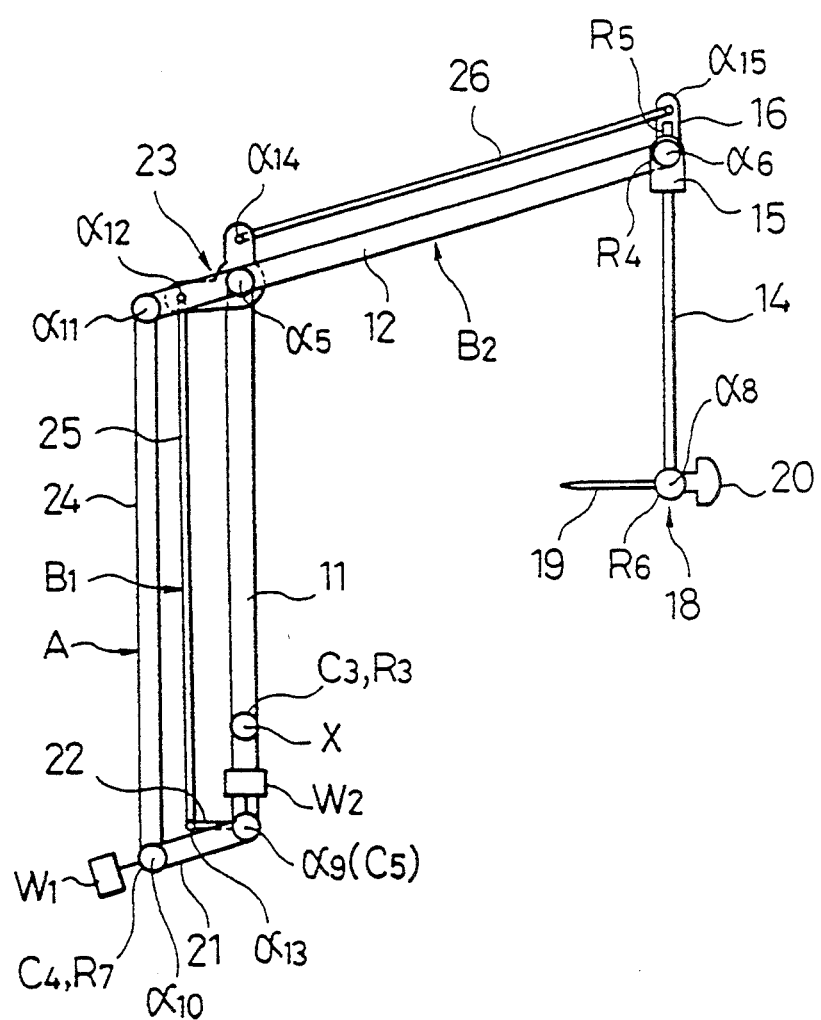
FIG. 4 shows schematically in side view the structure shown in FIG. 2, in which the second link is pivoted.
Figure 5:
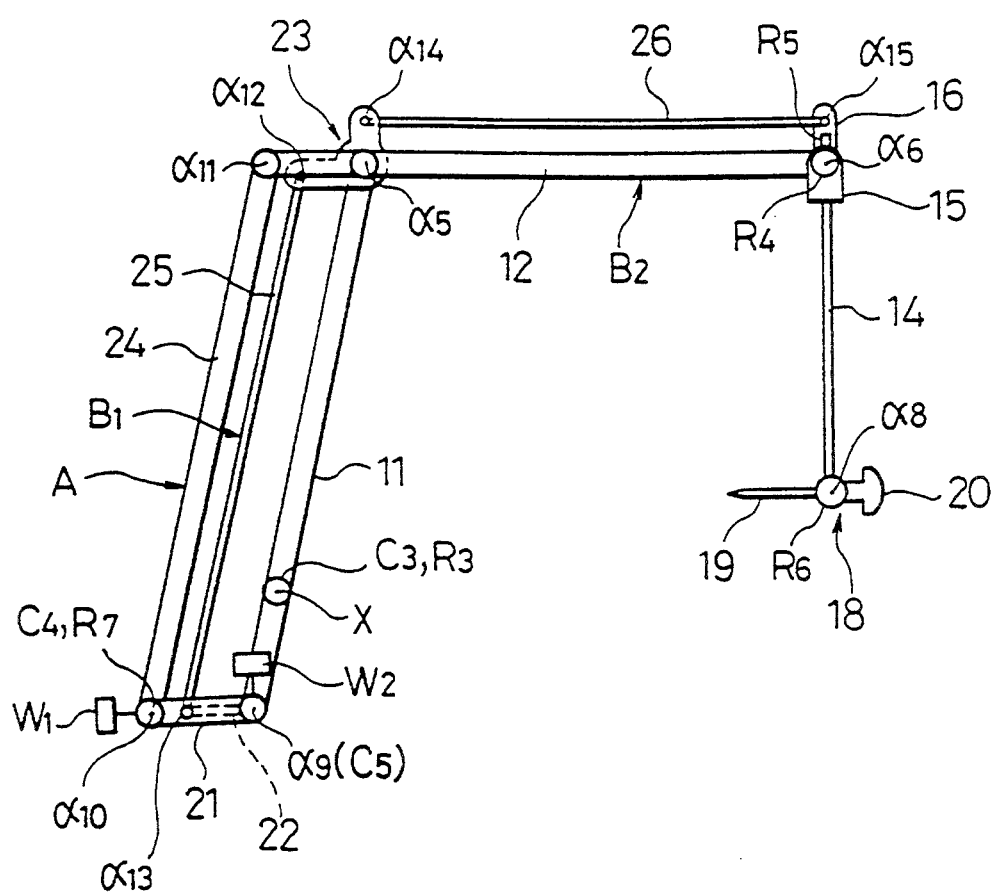
FIG. 5 shows schematically in side view the structure shown in FIG. 2, in which the first link is pivoted.

Next, when the second link 12 is pivoted upward on the connecting shaft $\alpha_5$, as shown in FIG. 4, the shape of the main parallel link A and the second subsidiary parallel link $B_2$ are modified, and the amount of modification (i.e. the pivoted angle of the second link 12) can be detected by the rotary encoder $R_7$ disposed to the connection shaft $\alpha_{10}$. Since the crank member 23 is not pivoted in this process, the vertical posture of the third link 14 can be maintained as such. Incidentally, this motion can be locked by the magnetic clutch $C_4$. Further, the second link 12 can be operated with a small operating physical force with the aid of the first counter weight $W_1$.

Subsequently, when the first link 11 is pivoted on the pivot X to modify the shape of the main parallel link A so as to bring the third link 14 farther, the pivoted angle of the first link 11 (the shift of the indicating unit 18) can be detected by the rotary encoder $R_7$. This motion can be locked by the magnetic clutch $C_4$. Further, the first link 11 can also be operated with a small operating physical force with the aid of the first counter weight $W_1$. Besides, since the crank member 23 is not pivoted either in this process, the vertical posture of the third link 14 can be maintained as such.

Meanwhile, the rotational amount of the third link 14 on the longitudinal axis $\alpha_7$ thereof can be detected by the rotary encoder $R_5$, while the pivoted angle of the indicating unit 18 can be detected by the rotary encoder Accordingly, the location of the tip of the indicating unit 18 can be detected based on the signals from the respective rotary encoders $R_1$ to $R_7$, so that the tip of the indicating unit 18 can be guided to the desired point based on the positional information from the CT scanner and the like. Besides, in the apparatus according to this embodiment, while the respective links can be operated freely on the pivot X and on the other connection shafts $\alpha_5 \ldots$, the motions thereof can be locked by the magnetic clutches $C_3$ to $C_5$ disposed therebelow respectively. Accordingly, no heavy clutch means is needed to be disposed to the connection shaft $\alpha_6$ which is brought close to the head of the patient P, providing excellent operability and stability.

The constitution of the medical locating apparatus according to this invention is as described above, and the main parallel link and the subsidiary parallel links are formed by the first to third links, the first to third sub-links and the crank member, in which the respective links are interlocked with the corresponding parallel links, respectively. Accordingly, clutch means need not be disposed to all of the connection shafts of the links, but they may be disposed only to the pivot locating relatively at a low position, to the connection shaft connecting the first auxiliary link with the first sub-link and to the connection shaft connecting the second auxiliary link with the second sub-link. Thus, the links need not be operated by the respective heavy clutches, the present apparatus enjoys excellent operability, and such constitution is also preferred from the standpoint of stability of the entire apparatus.

Further, the angles of the links are detected by rotary encoders which require no A/D conversion and are not affected by the temperature changes, the present apparatus also enjoys excellent locating accuracy.

Moreover, since the first counterweight, which is disposed to protrude horizontally from the other end portion of the first auxiliary link to protrude and can be pivoted interlocking therewith, and the second counterweight, which is disposed to protrude upward from one end portion of the second auxiliary link and can be interlocked therewith are provided, respectively, the links can be operated with a very small physical force, providing excellent operability.

What is claimed is:

1. A medical locating apparatus, comprising:
   a first support;
   an elongate first link pivotally supported intermediate its ends by a pivot operatively connected to said first support;
   a second link pivotally connected to an upper end portion of said first link;
   a third link pivotally connected to a distal end portion of said second link, and rotatable about a longitudinal axis;
   a connection shaft connecting said first link with said second link;
   a crank member pivotally connected to said connection shaft;
   a first auxiliary link and a second auxiliary link, both pivotally connected to respective first end portions to a lower end portion of said first link;
   a first sub-link, disposed to be parallel with said first link, connecting a second end portion of said first auxiliary link with a proximal end portion of said second auxiliary link;
   a second sub-link, disposed to be parallel with said first link, connecting a second end portion of said second auxiliary link to a first end portion of said crank member;
   a third sub-link, disposed to be parallel with said second link, connecting a proximate end portion of said third link with a second end portion of said crank member;
   an indicating unit mounted at a lower end of the third link;
   a first magnetic clutch and a first rotary encoder provided on said pivot and a second magnetic clutch and a second rotary encoder on a connection shaft connecting said first auxiliary link with said first sub-link for enabling selected rotational engagements thereat;
   a third magnetic clutch provided on a connection shaft connecting said second auxiliary link with said second sub-link for enabling engagement therebetween; and
   a rotary encoder provided on each of a connection shaft connecting said second link with said third link, third link along its longitudinal axis, and a rotary shaft of said indicating unit for providing outputs corresponding to their respective, rotational orientations.

2. The medical locating apparatus according to claim 1, wherein:

a first counterweight is provided one the second end portion of said first auxiliary link to protrude horizontally therefrom and a second counterweight is provided one the first end portion of said second auxiliary link to protrude upwardly therefrom;

said first counterweight and said second counterweight interlocking with said first auxiliary link and said second auxiliary link, respectively.

* * * * *

UNITED STATES PATENT AND TRADEMARK OFFICE
CERTIFICATE OF CORRECTION

PATENT NO. : 5,441,505
DATED : August 15, 1995
INVENTOR(S) : Katsushige Nakamura It is certified that error appears in the above-indentified patent and that said Letters Patent is hereby corrected as shown below:

Column 6, line 45, delete "auxiliary";
Column 6, line 68, before "third link" insert --the--.
Column 7, line 6, change "one" to --on--.
Column 8, line 2, change "one" to --on--.

Signed and Sealed this

Twenty-fourth Day of October, 1995

Attest:

BRUCE LEHMAN

Attesting Officer

Commissioner of Patents and Trademarks